(12) United States Patent
Gilliam et al.

(10) Patent No.: US 6,561,990 B1
(45) Date of Patent: May 13, 2003

(54) ISOKINETIC TESTING MACHINE

(76) Inventors: Thomas B. Gilliam, 2047 Fairway Blvd., Hudson, OH (US) 44236; Robert L. Wells, 1121 Wood Rd., DeWitt, MI (US) 48820

( * ) Notice: Subject to any disclaimer, the term of this patent is extended or adjusted under 35 U.S.C. 154(b) by 0 days.

(21) Appl. No.: 09/471,874

(22) Filed: Dec. 23, 1999

(51) Int. Cl.[7] .............................................. A61B 5/103
(52) U.S. Cl. ........................ 600/587; 482/51; 482/908
(58) Field of Search ................................. 600/587, 588, 600/589, 590, 591, 592, 593, 594, 595; 482/51–80, 91–133, 908, 910

(56) References Cited

U.S. PATENT DOCUMENTS

| | | | | |
|---|---|---|---|---|
| 4,462,252 A | * | 7/1984 | Smidt et al. | 73/379 |
| 4,732,381 A | * | 3/1988 | Skowronski | 272/134 |
| 5,331,851 A | * | 7/1994 | Parviainen et al. | 73/379.01 |

* cited by examiner

*Primary Examiner*—Kevin Shaver
*Assistant Examiner*—Pamela Wingood
(74) *Attorney, Agent, or Firm*—Hahn Loeser & Parks LLP

(57) ABSTRACT

An isokinetic testing machine which includes an adjustable seat which is capable of being positioned to accommodate individuals of different sizes for various isokinetic tests of the legs, arms and/or back and a moveable dynamometer which is capable of being positioned to measure left knee strength, right knee strength, left elbow strength, right elbow strength and/or trunk movement. In one preferred embodiment of the present invention, the isokinetic machine is fabricated in two (2) independent sections which are capable of being readily disassembled for transportation and reassembled at remote locations for on-site isokinetic testing.

21 Claims, 18 Drawing Sheets

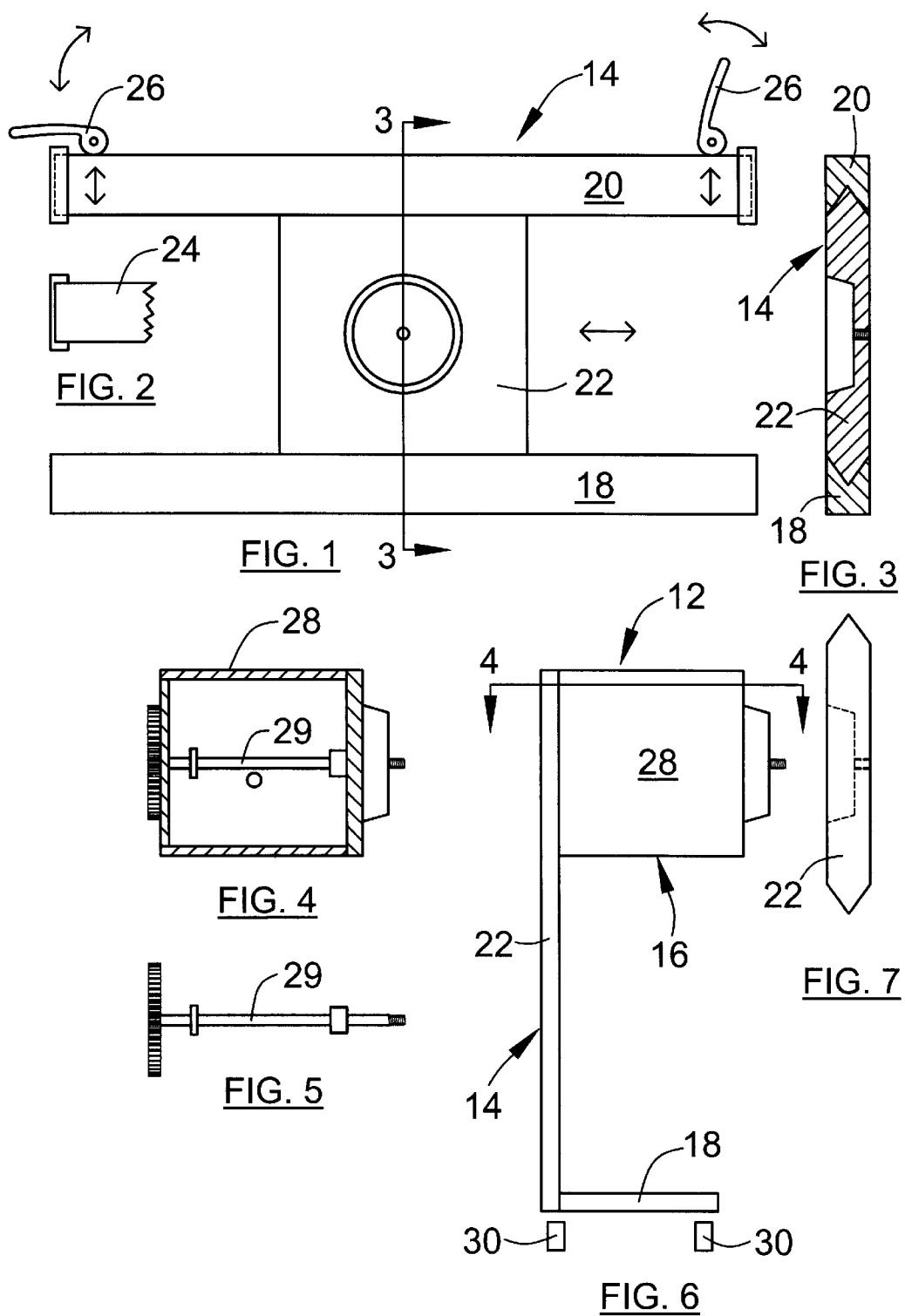

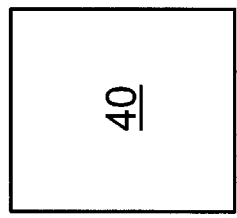
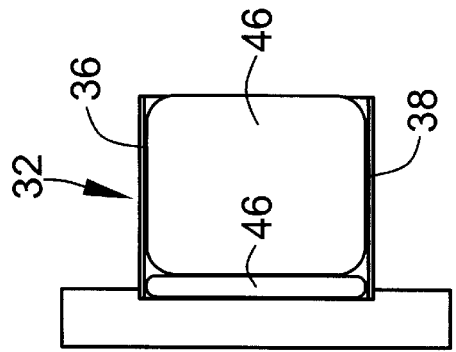
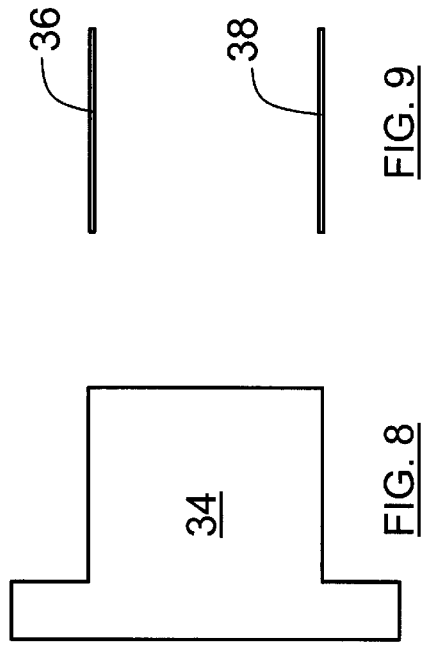
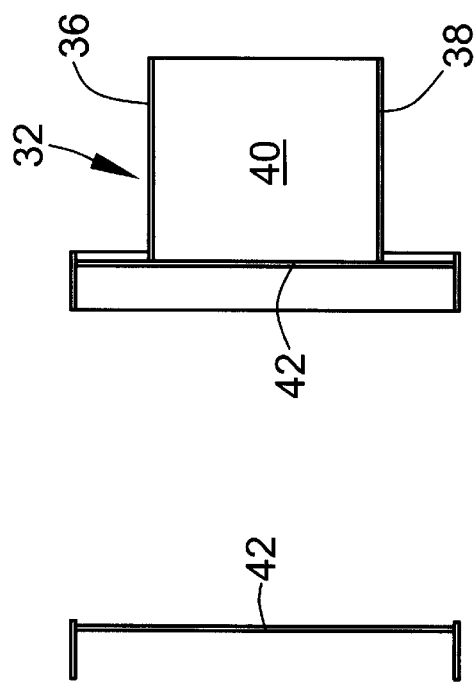

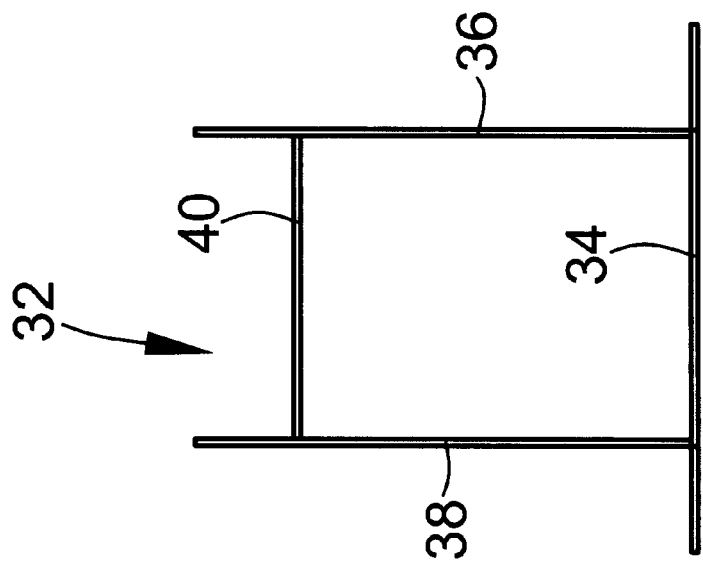
FIG. 17
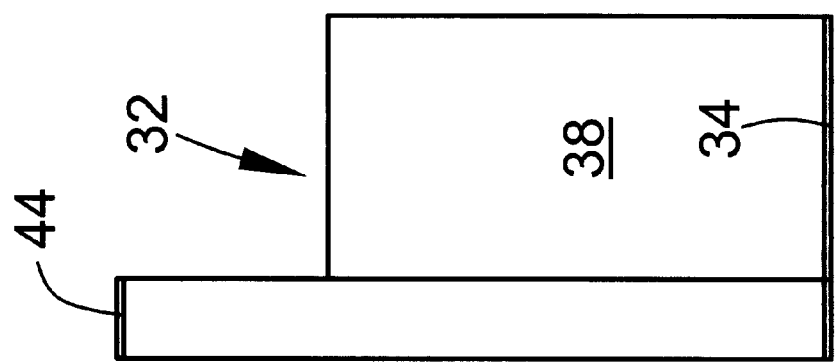
FIG. 16
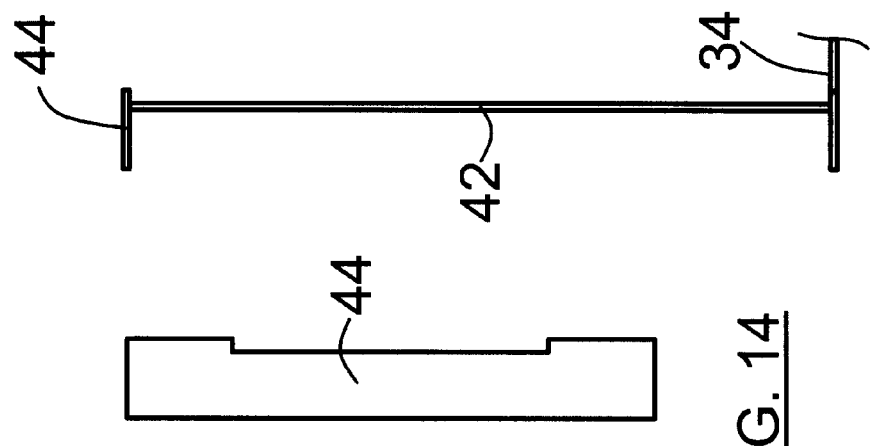
FIG. 15
FIG. 14

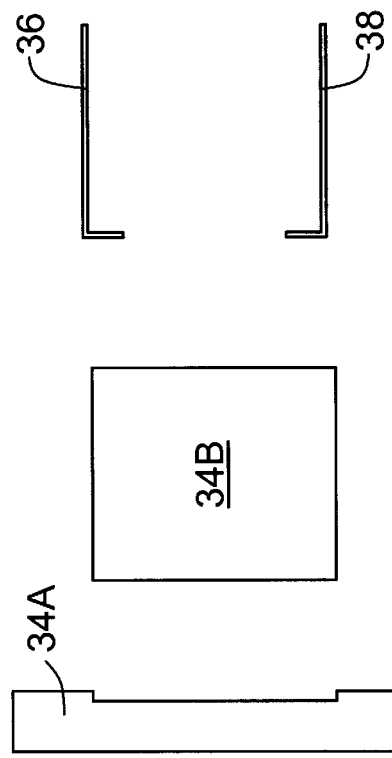
FIG. 19
FIG. 18
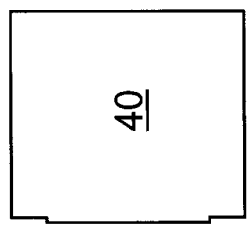
FIG. 21
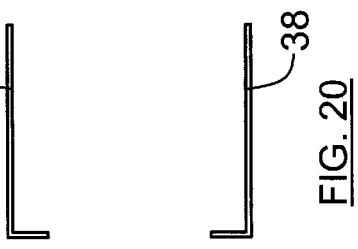
FIG. 20
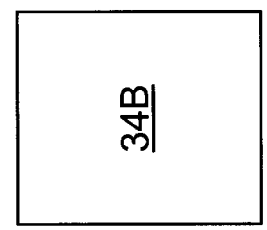
FIG. 23
FIG. 22
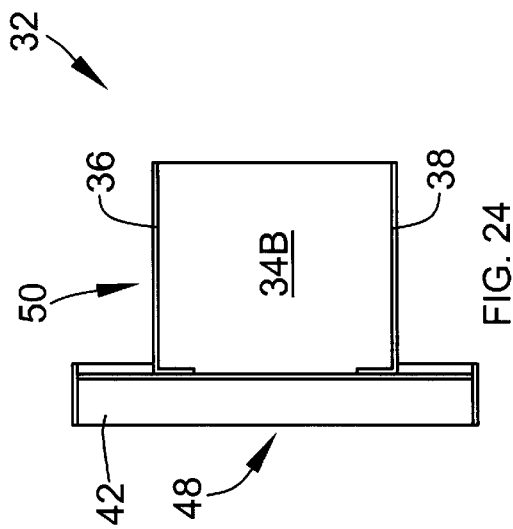
FIG. 24

US 6,561,990 B1

ISOKINETIC TESTING MACHINE

BACKGROUND AND SUMMARY OF THE INVENTION

The present invention relates generally to a new and novel isokinetic testing machine. More particularly, the present invention relates to an isokinetic testing machine which is compact and capable of being readily set up, used, disassembled and transported to and from remote locations for isokinetic testing.

In the field of isokinetic testing, it has been customary for patients and other individuals being tested to go to a hospital or some other medical facility to have isokinetic testing performed. Known prior art isokinetic testing machines are relatively large and difficult to transport and thus, are not commonly moved once positioned at a particular location. Accordingly, if multiple individuals working for a certain employer, for example, are to be tested, they must all travel to the location of the isokinetic testing machine for evaluation. This can be costly for the employer and inconvenient and time consuming for the individuals being evaluated.

Accordingly, an object of the present invention is the provision of an isokinetic testing machine which is relatively compact and which can be readily set up, operated, disassembled and transported to remote locations to permit on-site isokinetic testing.

Another object of the present invention is to provide an isokinetic testing machine which is capable of conducting multiple isokinetic tests and which is readily convertible from one isokinetic test configuration to another isokinetic test configuration.

These and other objects of the present invention are attained by the provision of an isokinetic testing machine which includes an adjustable seat subsection which is capable of being positioned to accommodate individuals of different sizes for various isokinetic tests, an outer frame subsection around the adjustable seat subsection and a dynamometer subsection which is capable of locating a dynamometer in the appropriate position to conduct isokinetic tests on the left leg, the right leg, the left arm, the right arm and the trunk of an individual to be evaluated. In a preferred embodiment of the present invention, each of the three (3) isokinetic test machine subsections, the adjustable seat subsection, the outer frame subsection and the dynamometer subsection, are fabricated as separate independent subassemblies, which are capable of being readily disassembled for transportation and assembled at remote locations for on-site isokinetic testing.

Other advantages and novel features of the present invention will become apparent in the following detailed description of the invention when considered in conjunction with the accompanying drawings.

BRIEF DESCRIPTION OF THE DRAWINGS

FIG. 1 is a side elevational view of a dynamometer subsection used in an isokinetic testing machine in accordance with a first preferred embodiment of the present invention.

FIG. 2 is a top sectional view of a harness strap and restraining clamp in the dynamometer subsection shown in FIG. 1 used in the isokinetic testing machine in accordance with a first preferred embodiment of the present invention.

FIG. 3 is a cross-sectional front view of the dynamometer subsection shown in FIG. 1 used in the isokinetic testing machine in accordance with a first preferred embodiment of the present invention taken across line 3—3 in FIG. 1.

FIG. 4 is a top cross-sectional view of the dynamometer subsection shown in FIG. 1 used in the isokinetic testing machine in accordance with a first preferred embodiment of the present invention taken across line 4—4 in FIG. 6.

FIG. 5 is a side elevational view of an elongated rotatable rod member in the dynamometer subsection shown in FIG. 1 used in the isokinetic testing machine in accordance with a first preferred embodiment of the present invention.

FIG. 6 is a front elevational view of the dynamometer subsection shown in FIG. 1 used in the isokinetic testing machine in accordance with a first preferred embodiment of the present invention.

FIG. 7 is a front view of a dynamometer mounting plate in the dynamometer subsection shown in FIG. 1 used in the isokinetic testing machine in accordance with a first preferred embodiment of the present invention taken across line 3—3 in FIG. 1.

FIG. 8 is a top plan view of a base member in an adjustable seat subsection shown in FIG. 12 used in the isokinetic testing machine in accordance with a first preferred embodiment of the present invention.

FIG. 9 is a top plan view of a first side member and a second side member in the adjustable seat subsection shown in FIG. 12 used in the isokinetic testing machine in accordance with a first preferred embodiment of the present invention.

FIG. 10 is a top plan view of a horizontal seat member in the adjustable seat subsection shown in FIG. 12 used in the isokinetic testing machine in accordance with the first preferred embodiment of the present invention.

FIG. 11 is a top plan view of a vertical back member, a first side support member and a second side support member in the adjustable seat subassembly shown in FIG. 12 used in the isokinetic testing machine in accordance with a first preferred embodiment of the present invention.

FIG. 12 is a top plan view of the adjustable seat subsection used in the isokinetic testing machine in accordance with a first preferred embodiment of the present invention.

FIG. 13 is a top plan view of the adjustable seat subsection shown in FIG. 12 with pads positioned on the horizontal seat member and the vertical back member for user comfort used in the isokinetic testing machine in accordance with a first preferred embodiment of the present invention.

FIG. 14 is a top plan view of a horizontal top member in the adjustable seat subsection shown in FIG. 12 used in the isokinetic testing machine in accordance with a first preferred embodiment of the present invention.

FIG. 15 is a side elevational view of the horizontal top member, the vertical back member and the base member in the adjustable seat subsection shown in FIG. 12 used in the isokinetic testing machine in accordance with a first preferred embodiment of the present invention.

FIG. 16 is a side elevational view of the adjustable seat subsection shown in FIG. 12 used in the isokinetic testing machine in accordance with a first preferred embodiment of the present invention.

FIG. 17 is a front elevational view of the adjustable seat subsection shown in FIG. 12 used in the isokinetic testing machine in accordance with a first preferred embodiment of the present invention.

FIG. 18 is a top plan view of a first base member in an adjustable seat subsection shown in FIG. 24 used in an isokinetic testing machine in accordance with a second preferred embodiment of the present invention.

FIG. 19 is a top plan view of a second base member in the adjustable seat subsection shown in FIG. 24 used in the isokinetic testing machine in accordance with a second preferred embodiment of the present invention.

FIG. 20 is a top plan view of a first side member and a second side member in the adjustable seat subsection shown in FIG. 24 used in the isokinetic testing machine in accordance with a second preferred embodiment of the present invention.

FIG. 21 is a top plan view of a horizontal seat member in the adjustable seat subsection shown in FIG. 24 used in the isokinetic testing machine in accordance with a second preferred embodiment of the present invention.

FIG. 22 is a top plan view of the first base member, a first side support member, a second side support member and a vertical back member in the adjustable seat subsection shown in FIG. 24 used in the isokinetic testing machine in accordance with a second preferred embodiment of the present invention.

FIG. 23 is a top plan view of the second base member, the first side member and the second side member in the adjustable seat subsection shown in FIG. 24 used in the isokinetic testing machine in accordance with a second preferred embodiment of the present invention.

FIG. 24 is a top plan view of the adjustable seat subsection used in the isokinetic testing machine in accordance with a second preferred embodiment of the present invention.

DETAILED DESCRIPTION OF THE DRAWINGS

Figure 25:
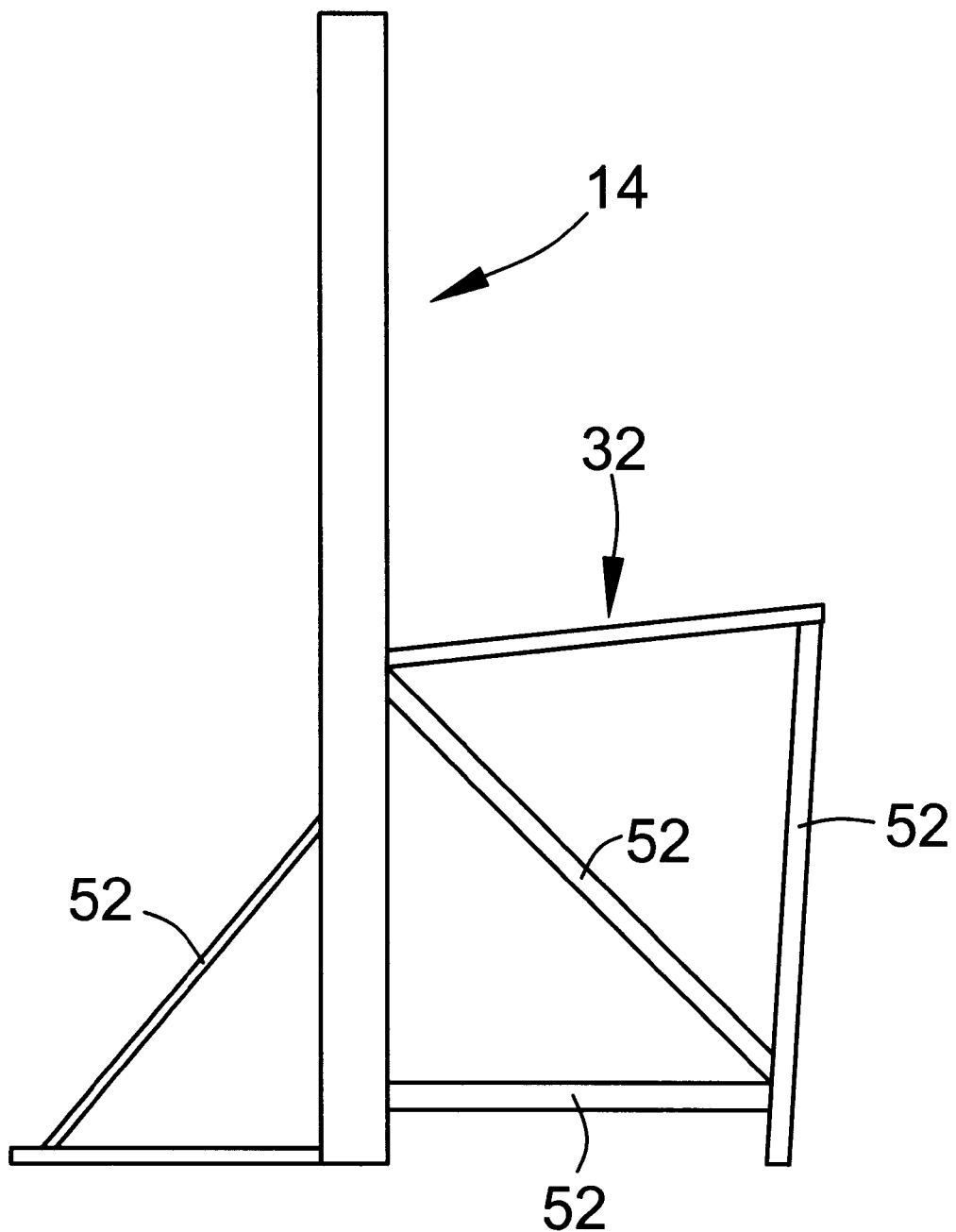
FIG. 25 is a side elevational view of an outer frame subsection and an adjustable seat subsection used in an isokinetic testing machine in accordance with a third preferred embodiment of the present invention.
Figure 27:
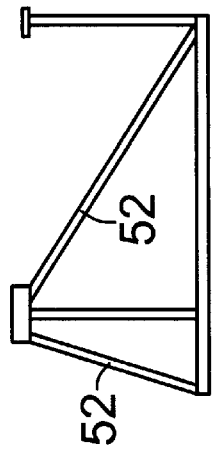
FIG. 27 is a side elevational view of the outer frame subsection and the adjustable seat subsection shown in FIG. 25 used in the isokinetic testing machine in accordance with a third preferred embodiment of the present invention.
Figure 26:
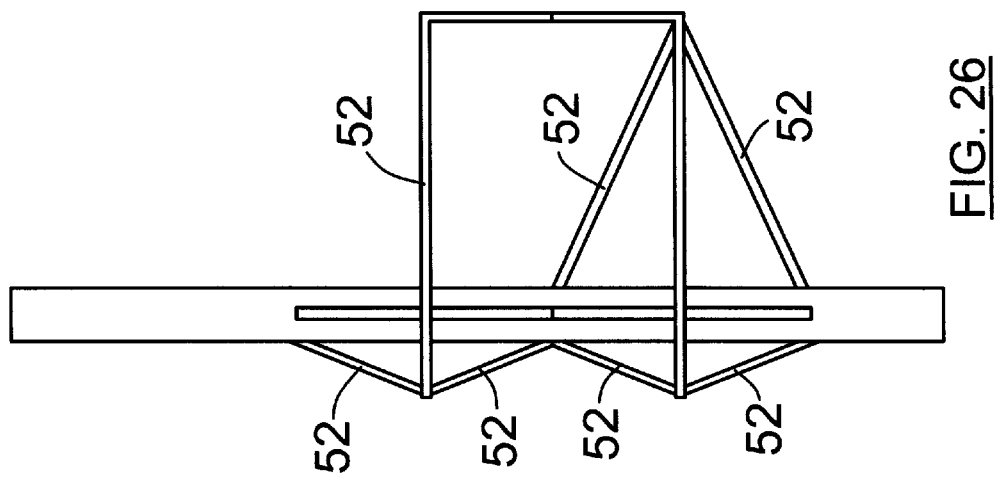
FIG. 26 is a top plan view of the outer frame subsection and the adjustable seat subsection shown in FIG. 25 used in the isokinetic testing machine in accordance with a third preferred embodiment of the present invention.
Figure 28:
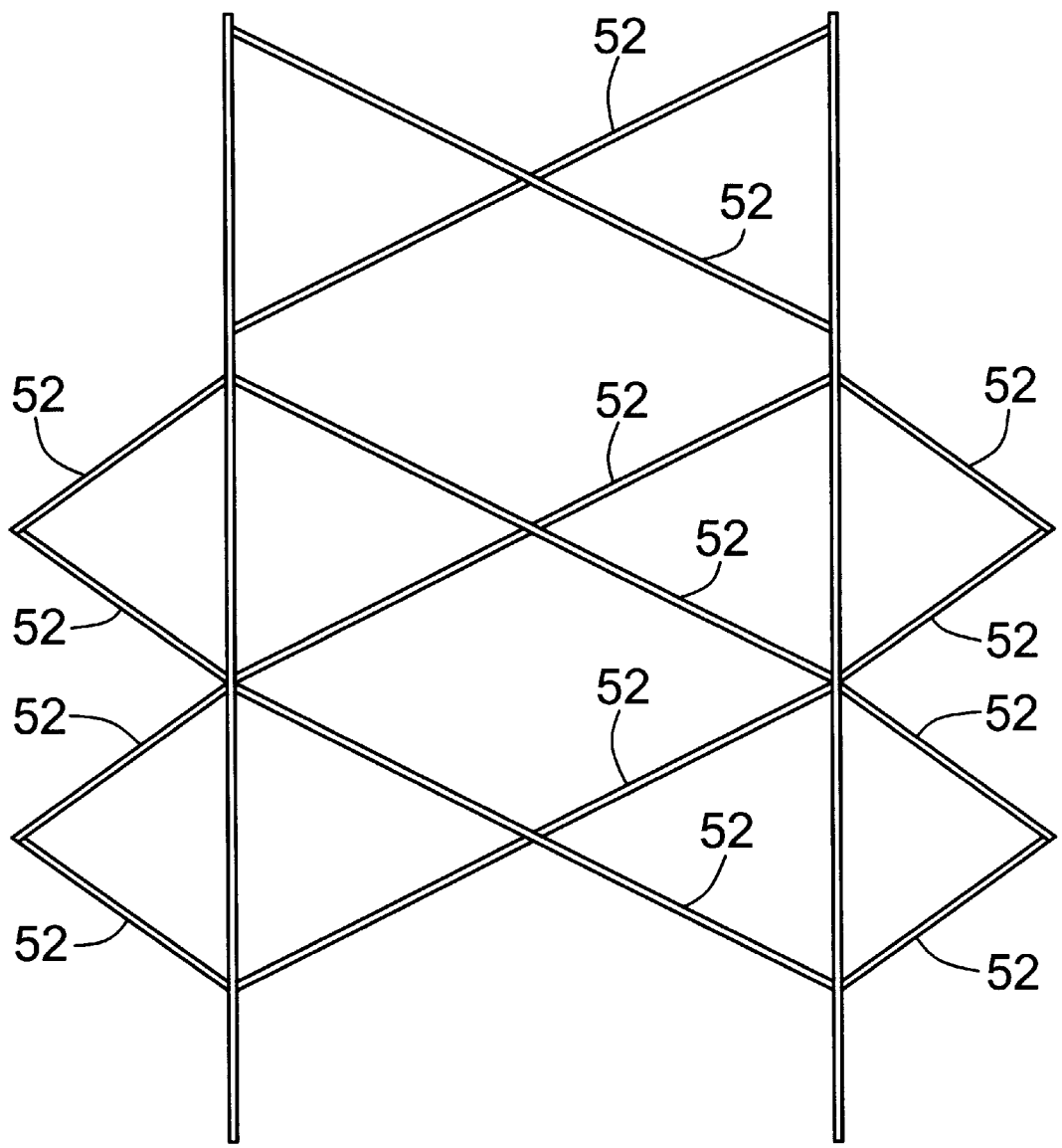
FIG. 28 is a top plan view of the outer frame subsection and the adjustable seat subsection shown in FIG. 25 used in the isokinetic testing machine in accordance with a third preferred embodiment of the present invention.

In the following detailed description of a first preferred embodiment of the present invention, a second preferred embodiment of the present invention and a third preferred embodiment of the present invention, reference is made to the accompanying drawings which, in conjunction with this detailed description, illustrate and describe a first preferred embodiment, a second preferred embodiment and a third preferred embodiment of an isokinetic testing machine in accordance with the present invention. Referring first to FIGS. 1 through 7, which show a side elevational view of a dynamometer subsection used in an isokinetic testing machine in accordance with a first preferred embodiment of the present invention, a top sectional view of a harness strap and restraining clamp in the dynamometer subsection shown in FIG. 1 used in the isokinetic testing machine in accordance with a first preferred embodiment of the present invention, a cross-sectional front view of the dynamometer subsection shown in FIG. 1 used in the isokinetic testing machine in accordance with a first preferred embodiment of the present invention taken across line 3—3 in FIG. 1, a top cross-sectional view of the dynamometer subsection shown in FIG. 1 used in the isokinetic testing machine in accordance with a first preferred embodiment of the present invention taken across line 4—4 in FIG. 6, a side elevational view of an elongated rotatable rod member in the dynamometer subsection shown in FIG. 1 used in the isokinetic testing machine in accordance with a first preferred embodiment of the present invention, a front elevational view of the dynamometer subsection shown in FIG. 1 used in the isokinetic testing machine in accordance with a first preferred embodiment of the present invention and a cross-sectional front view of a dynamometer mounting plate in the dynamometer subsection shown in FIG. 1 used in the isokinetic testing machine in accordance with a first preferred embodiment of the present invention taken across line 3—3 in FIG. 1, respectively, dynamometer subsection of isokinetic testing machine 10 is generally identified by the reference number 12. Dynamometer subsection 12 generally includes dynamometer subsection support assembly 14 and dynamometer 16.

Referring in particular to FIG. 1, dynamometer subsection support assembly 14 generally includes lower horizontally extending support rail 18, upper horizontally extending support rail 20 and vertically extending dynamometer support plate 22 positioned therebetween. Vertically extending dynamometer support plate 22 is slidably positioned in relation to upper horizontally extending support rail 18 and lower horizontally extending support rail 20 is capable of being "locked" in positioned by harness strap 24 and restraining clamps 26. Dynamometer 16 includes dynamometer housing or protective enclosure 28 and elongated rotatable rod member 29 to allow rotation, adjustment and "locking" of dynamometer 16 in the desired position. If desired, lower horizontally extending support rail 18 can include a plurality of wheels 30 to facilitate moving dynamometer subsection 12.

Referring next to FIGS. 8 through 17, which show a top plan view of a base member in an adjustable seat subsection shown in FIG. 12 used in the isokinetic testing machine in accordance with a first preferred embodiment of the present invention, a top plan view of a first side member and a second side member in the adjustable seat subsection shown in FIG. 12 used in the isokinetic testing machine in accordance with a first preferred embodiment of the present invention, a top plan view of a horizontal seat member in the adjustable seat subsection shown in FIG. 12 used in the isokinetic testing machine in accordance with the first preferred embodiment of the present invention, a top plan view of a vertical back member, a first side support member and a second side support member in the adjustable seat subassembly shown in FIG. 12 used in the isokinetic testing machine in accordance with a first preferred embodiment of the present invention, a top plan view of the adjustable seat subsection used in the isokinetic testing machine in accordance with a first preferred embodiment of the present invention, a top plan view of the adjustable seat subsection shown in FIG. 12 with pads positioned on the horizontal seat member and the vertical back member for user comfort used in the isokinetic testing machine in accordance with a first preferred embodiment of the present invention, a top plan view of a horizontal top member in the adjustable seat subsection shown in FIG. 12 used in the isokinetic testing machine in accordance with a first preferred embodiment of the present invention, a side elevational view of the horizontal top member, the vertical back member and the base member in the adjustable seat subsection shown in FIG. 12 used in the isokinetic testing machine in accordance with a first preferred embodiment of the present invention, is a side elevational view of the adjustable seat subsection shown in FIG. 12 used in the isokinetic testing machine in accordance with a first preferred embodiment of the present invention and a front elevational view of the adjustable seat subsection shown in FIG. 12 used in the isokinetic testing machine in accordance with a first preferred embodiment of the present invention, respectively, adjustable seat subsection, identified by reference number 32, generally includes base member 34, first side member 36, second side member 38, horizontal seat member 40 and vertical back member 42. First side member 36 and second side member 38 upwardly extend from base member 34 and support horizontal seat member 40. Vertical back member 42 is positioned at the rear of first side member 36, second side member 38 and horizontal seat member 40. If desired, horizontal top member 44 is positioned on the top of vertical back member 42 and pads or cushioning 46 are placed on the top surface of horizontal seat member 40 and/or vertical back member 42. Horizontal seat member 40 is preferably moveable forwardly and rearwardly, but is preferably fixed, and thus not adjustable, along its vertical axis.

Referring next to FIGS. 18 through 24, which show a top plan view of a first base member in an adjustable seat subsection shown in FIG. 24 used in an isokinetic testing machine in accordance with a second preferred embodiment of the present invention, a top plan view of a second base member in the adjustable seat subsection shown in FIG. 24 used in the isokinetic testing machine in accordance with a second preferred embodiment of the present invention, a top plan view of a first side member and a second side member in the adjustable seat subsection shown in FIG. 24 used in the isokinetic testing machine in accordance with a second preferred embodiment of the present invention, a top plan view of a horizontal seat member in the adjustable seat subsection shown in FIG. 24 used in the isokinetic testing machine in accordance with a second preferred embodiment of the present invention, a top plan view of the first base member, a first side support member, a second side support member and a vertical back member in the adjustable seat subsection shown in FIG. 24 used in the isokinetic testing machine in accordance with a second preferred embodiment of the present invention, a top plan view of the second base member, the first side member and the second side member in the adjustable seat subsection shown in FIG. 24 used in the isokinetic testing machine in accordance with a second preferred embodiment of the present invention and a top plan view of the adjustable seat subsection used in the isokinetic testing machine in accordance with a second preferred embodiment of the present invention, respectively, if desired, adjustable seat subsection 32 can be fabricated in two (2) sections, vertical back subassembly 48 which includes a first portion 34B of base member 34, vertical back member 42 and horizontal top member 44 and horizontal seat subassembly 50 which includes the remaining portion 34A of base member 34, first side member 36, second side member 38 and horizontal seat member 40. With this design, vertical back subassembly 48 and horizontal seat subassembly 50 are capable of being joined together using mechanical fasteners, such as bolts, for use and separated into two (2) separate independent components for transportation and storage.

Referring to FIGS. 25 through 28, which show a side elevational view of an outer frame subsection and an adjustable seat subsection used in an isokinetic testing machine in accordance with a third preferred embodiment of the present invention, a top plan view of the outer frame subsection and the adjustable seat subsection shown in FIG. 25 used in the isokinetic testing machine in accordance with a third preferred embodiment of the present invention, a side elevational view of the outer frame subsection and the adjustable seat subsection shown in FIG. 25 used in the isokinetic testing machine in accordance with a third preferred embodiment of the present invention and a top plan view of the outer frame subsection and the adjustable seat subsection shown in FIG. 25 used in the isokinetic testing machine in accordance with a third preferred embodiment of the present invention, respectively, dynamometer subsection support assembly 14 and/or adjustable seat subsection 32 can include structural supports, generally identified by reference number 52, if desired. Dynamometer subsection support assembly 14 and adjustable seat subsection 32 are preferably fabricated as separate independent components to facilitate transportability. In addition, dynamometer subsection support assembly 14 and adjustable seat subsection 32 are preferably fabricated from a strong and durable, but relatively light, structural material, such as aluminum, although other materials, such as other metallic, polymeric and/or composite type materials, may alternately be used if desired.

Figure 29:
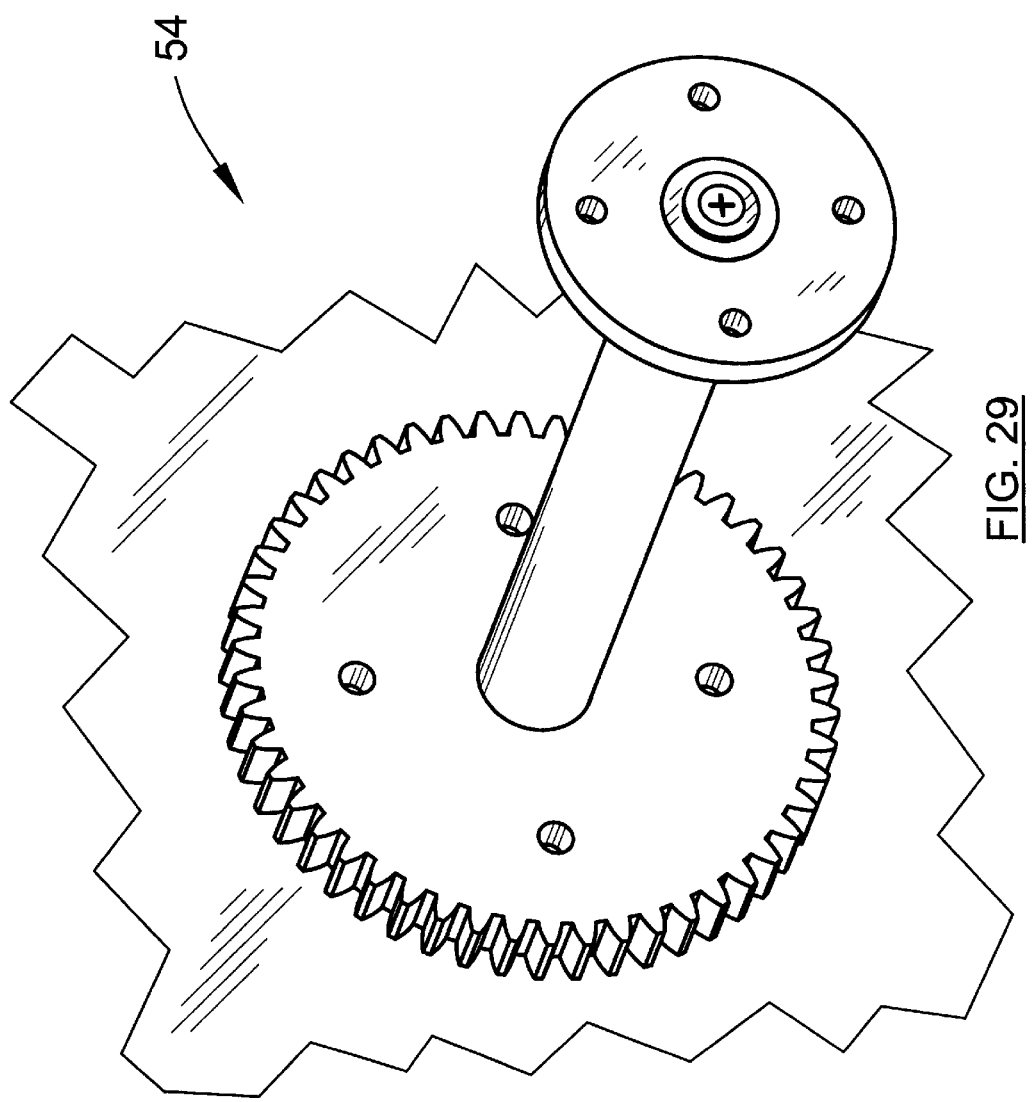
FIG. 29 is a perspective view of an attachment arrangement to attach the dynamometer in the dynamometer subsection shown in FIG. 1 used in the isokinetic testing machine in accordance with the present invention.
Figure 30:
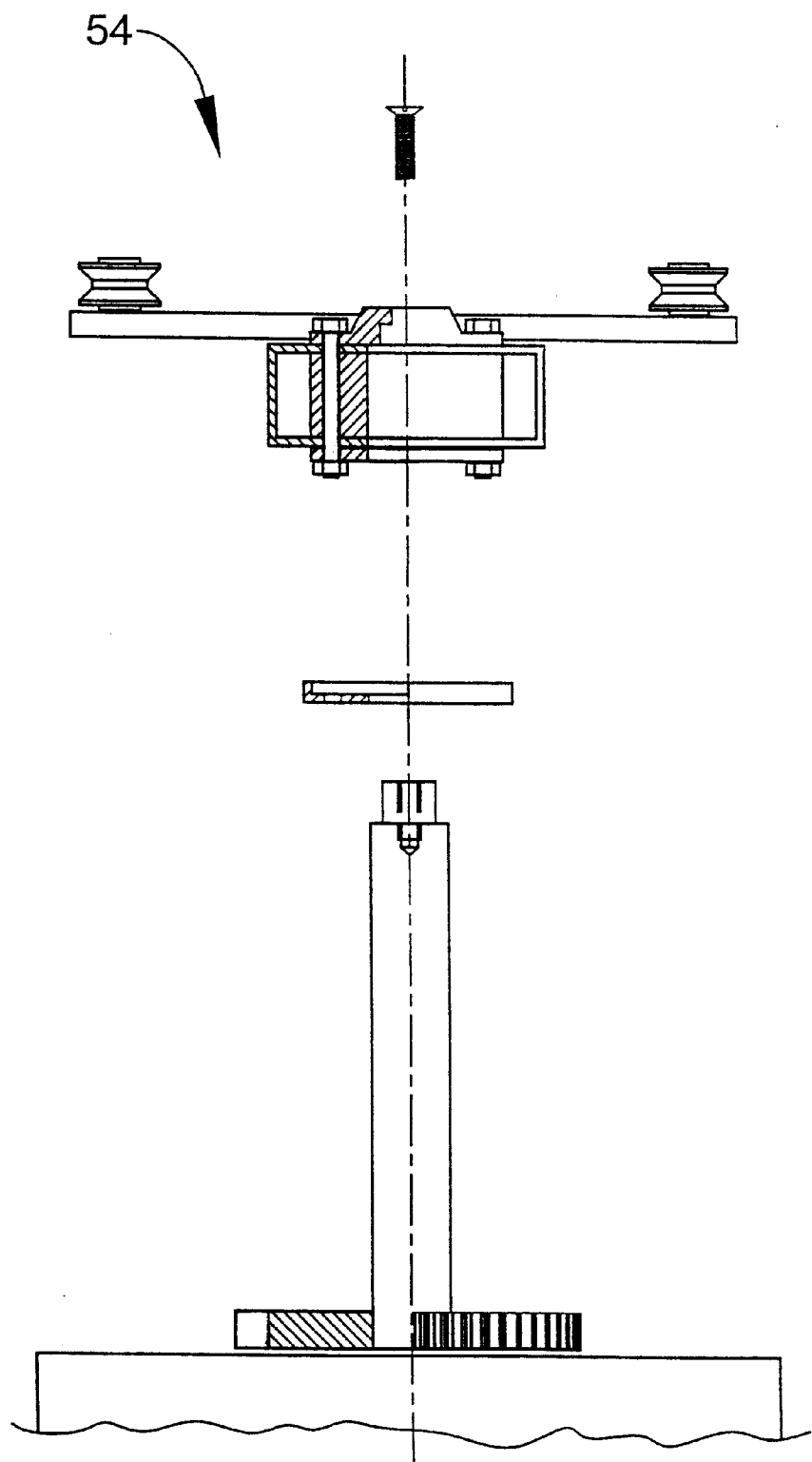
FIG. 30 is an exploded top plan view, shown partly in cross-section, of the attachment arrangement shown in FIG. 29 to attach the dynamometer in the dynamometer subsection shown in FIG. 1 used in the isokinetic testing machine in accordance with the present invention.

Referring to FIGS. 29 and 30, which show a perspective view of an attachment arrangement to attach the dynamometer in the dynamometer subsection shown in FIG. 1 used in the isokinetic testing machine in accordance with the present invention and an exploded top plan view, shown partly in cross-section, of the attachment arrangement shown in FIG. 29 to attach the dynamometer in the dynamometer subsection shown in FIG. 1 used in the isokinetic testing machine in accordance with the present invention, dynamometer attachment arrangement, generally identified by reference number 54, facilitates attachment of dynamometer 16 to dynamometer subsection support assembly 14.

Figure 31:
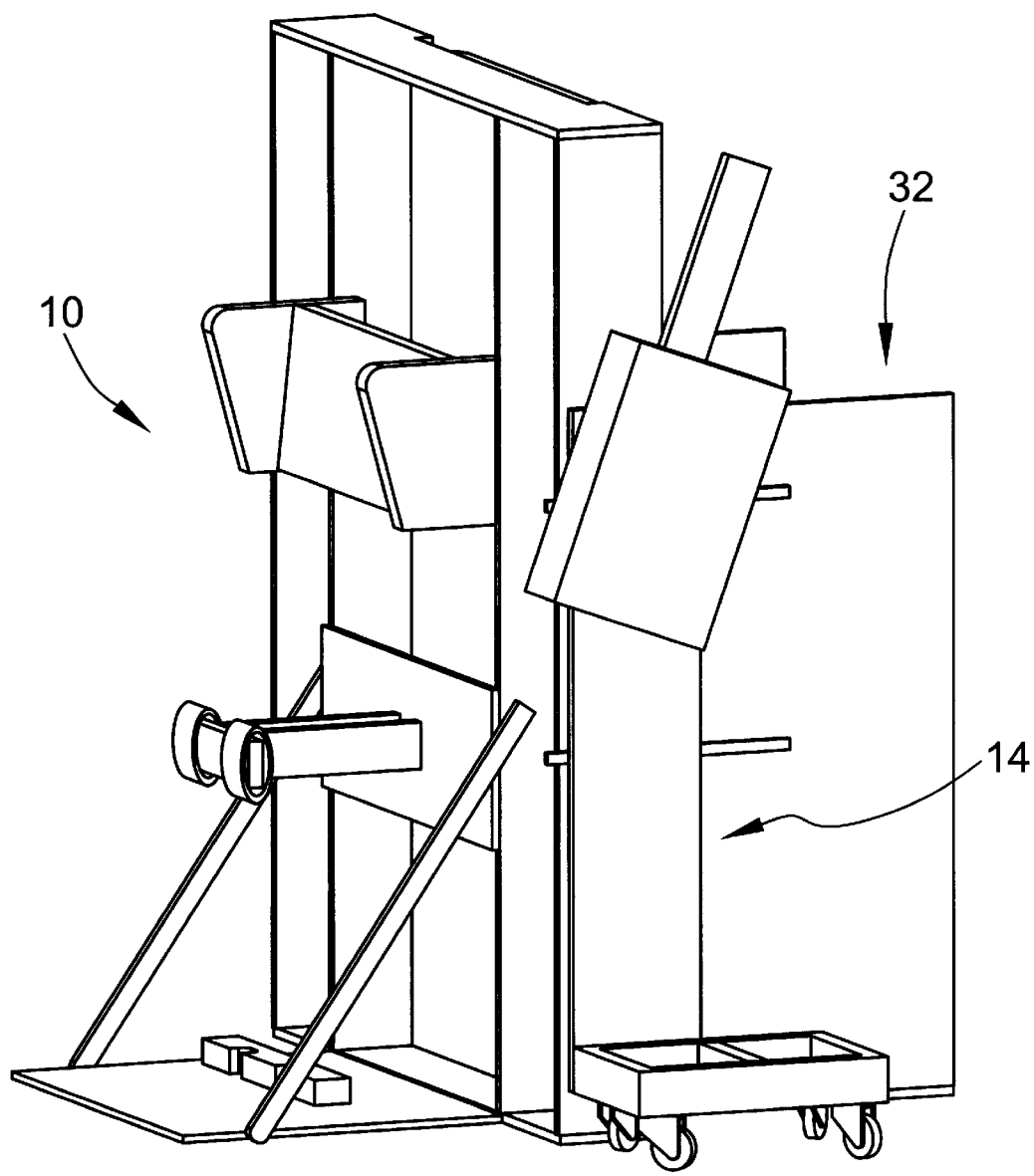
FIG. 31 is a perspective view of a wooden prototype of an isokinetic testing machine in accordance with the present invention showing the trunk isokinetic testing station.
Figure 32:
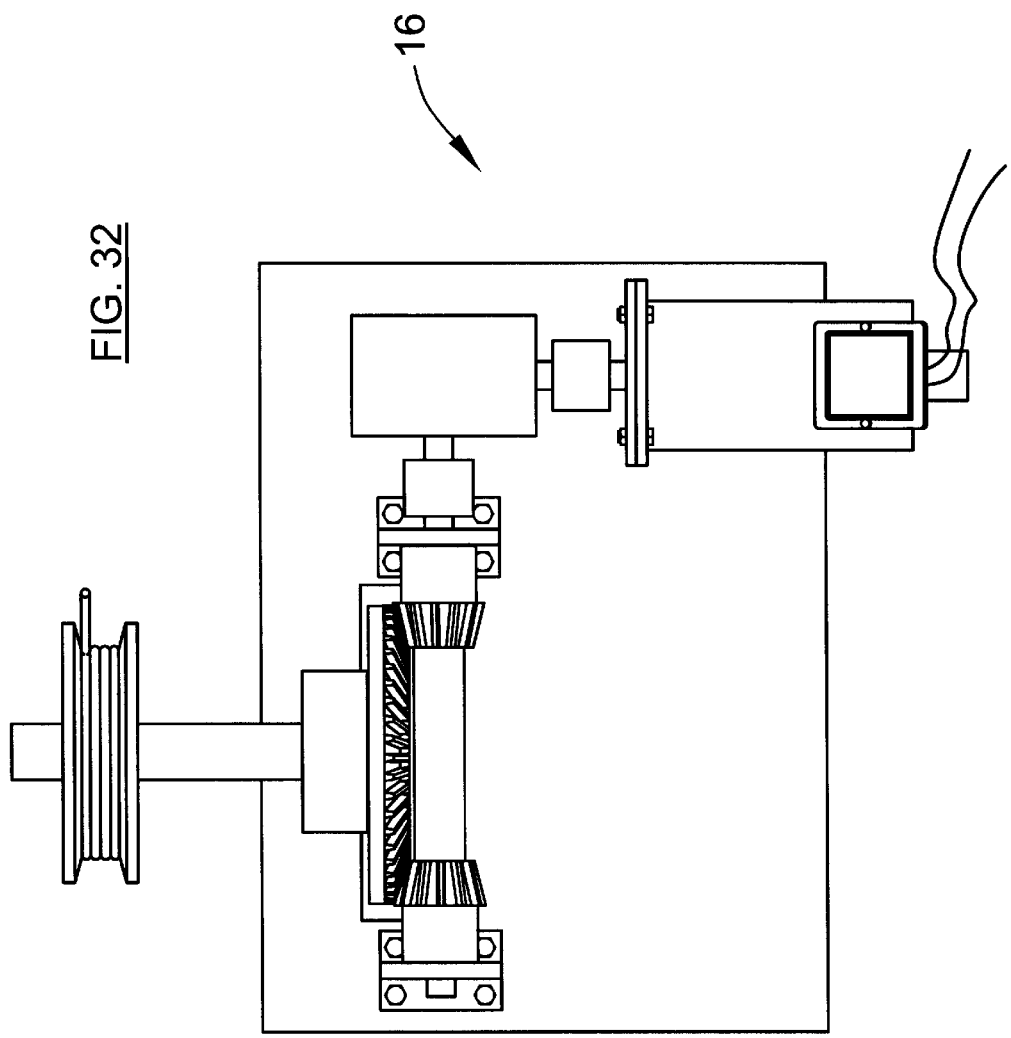
FIG. 32 is a top view of a dynamometer used in the isokinetic testing machine in accordance with the present invention.
Figure 33:
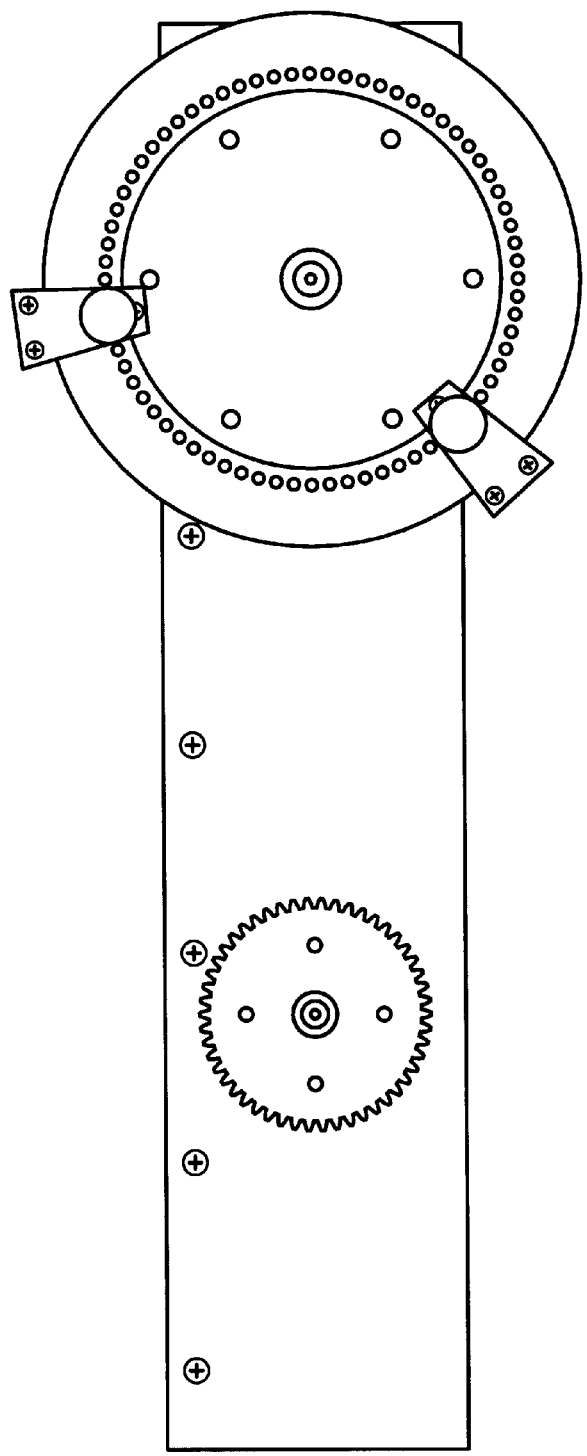
FIG. 33 is a plan view of a front plate of the dynamometer gear box shown in FIG. 34 showing range of motion stops and a rotational shaft for a pedestal used in the isokinetic testing machine in accordance with the present invention.

Referring next to FIG. 31, which shows a perspective view of a wooden prototype of an isokinetic testing machine in accordance with the present invention showing the trunk isokinetic testing station.

Figure 34:
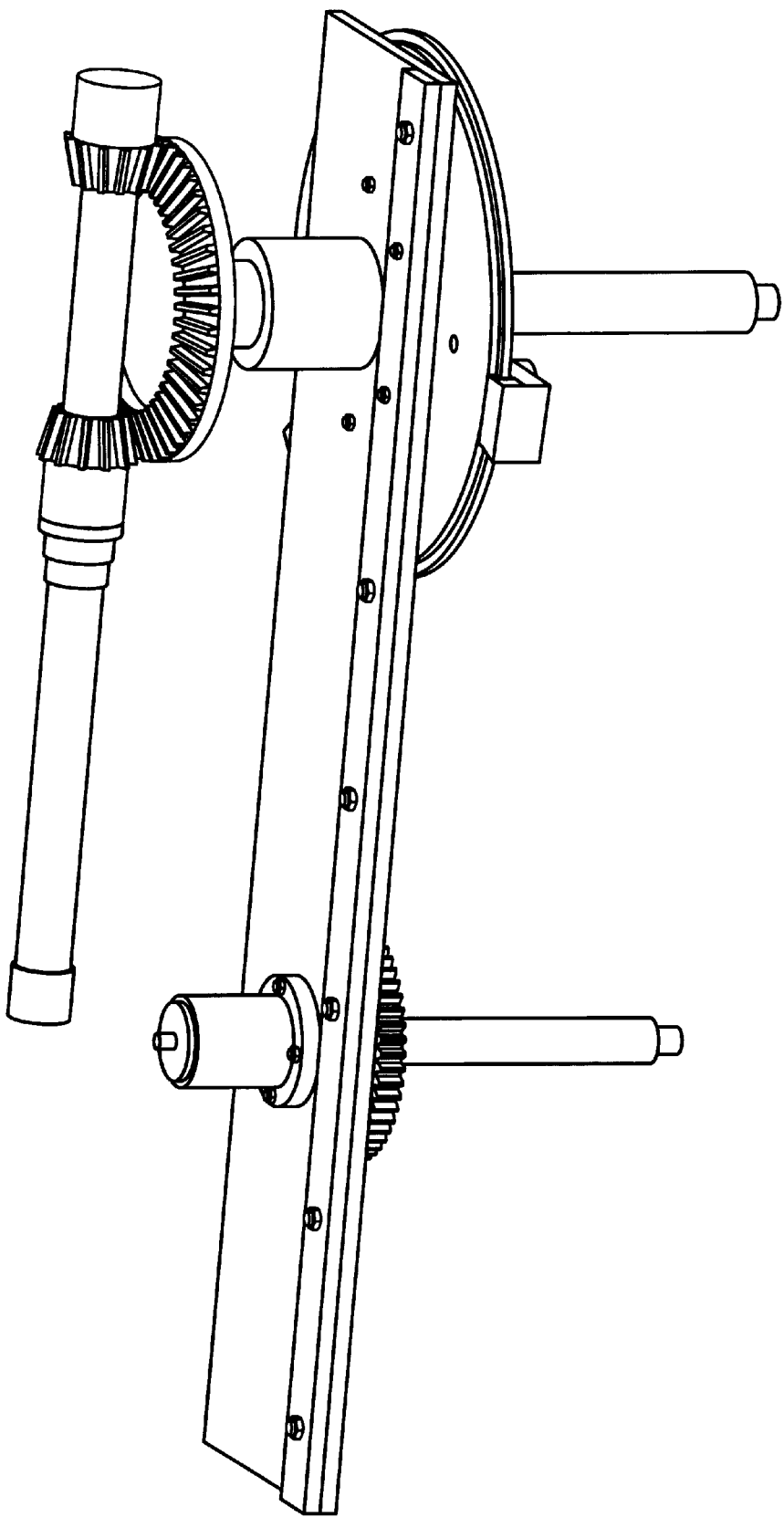
FIG. 34 is a first perspective view of a dynamometer gear box used in the isokinetic testing machine in accordance with the present invention.
Figure 35:
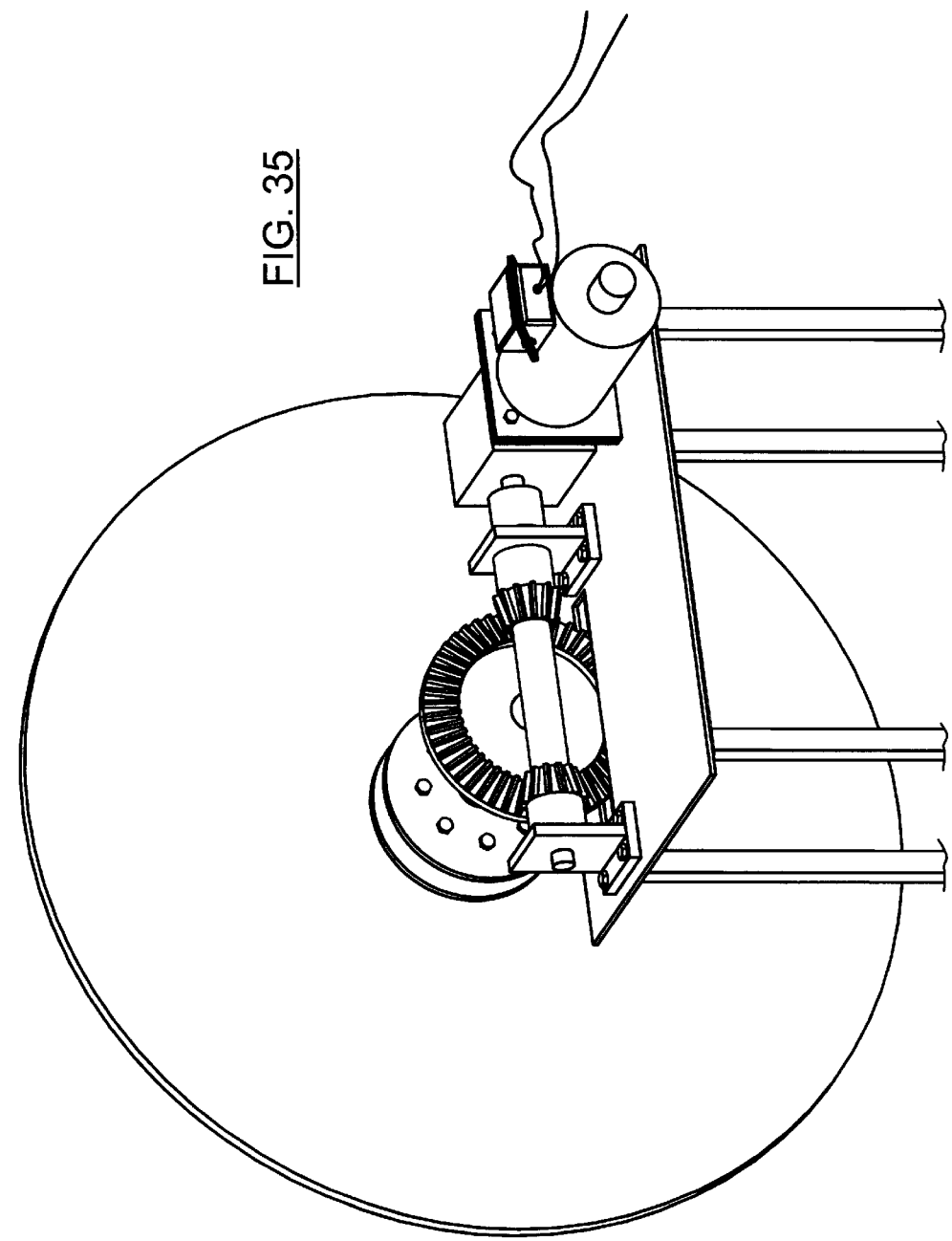
FIG. 35 is a second perspective view of the dynamometer gear box shown in FIG. 34 used in the isokinetic testing machine in accordance with the present invention.

Referring next to FIGS. 32 through 35, which show a top view of a dynamometer used in the isokinetic testing machine in accordance with the present invention, plan view of a front plate of the dynamometer gear box shown in FIG. 34 showing range of motion stops and a rotational shaft for a pedestal used in the isokinetic testing machine in accordance with the present invention, a first perspective view of a dynamometer gear box used in the isokinetic testing machine in accordance with the present invention and a second perspective view of the dynamometer gear box shown in FIG. 34 used in the isokinetic testing machine in accordance with the present invention, respectively, dynamometer subsection support assembly 14 facilitates the movement and positioning of dynamometer 16 to carry out the desired isometric tests.

Figure 36:
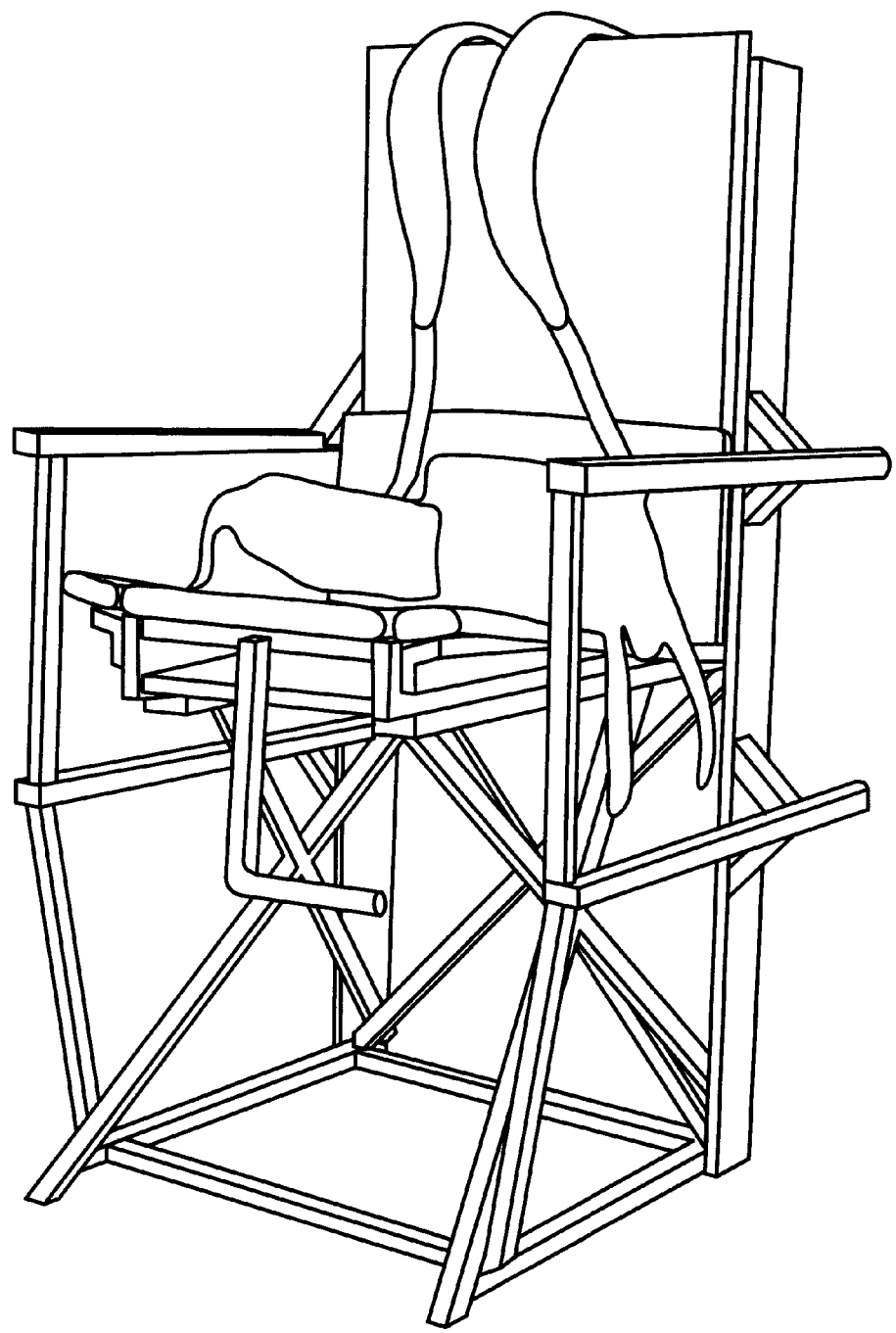
FIG. 36 is a first front perspective view of an outer frame subsection and an adjustable seat subsection fabricated from aluminum used in the isokinetic testing machine in accordance with the present invention.
Figure 37:
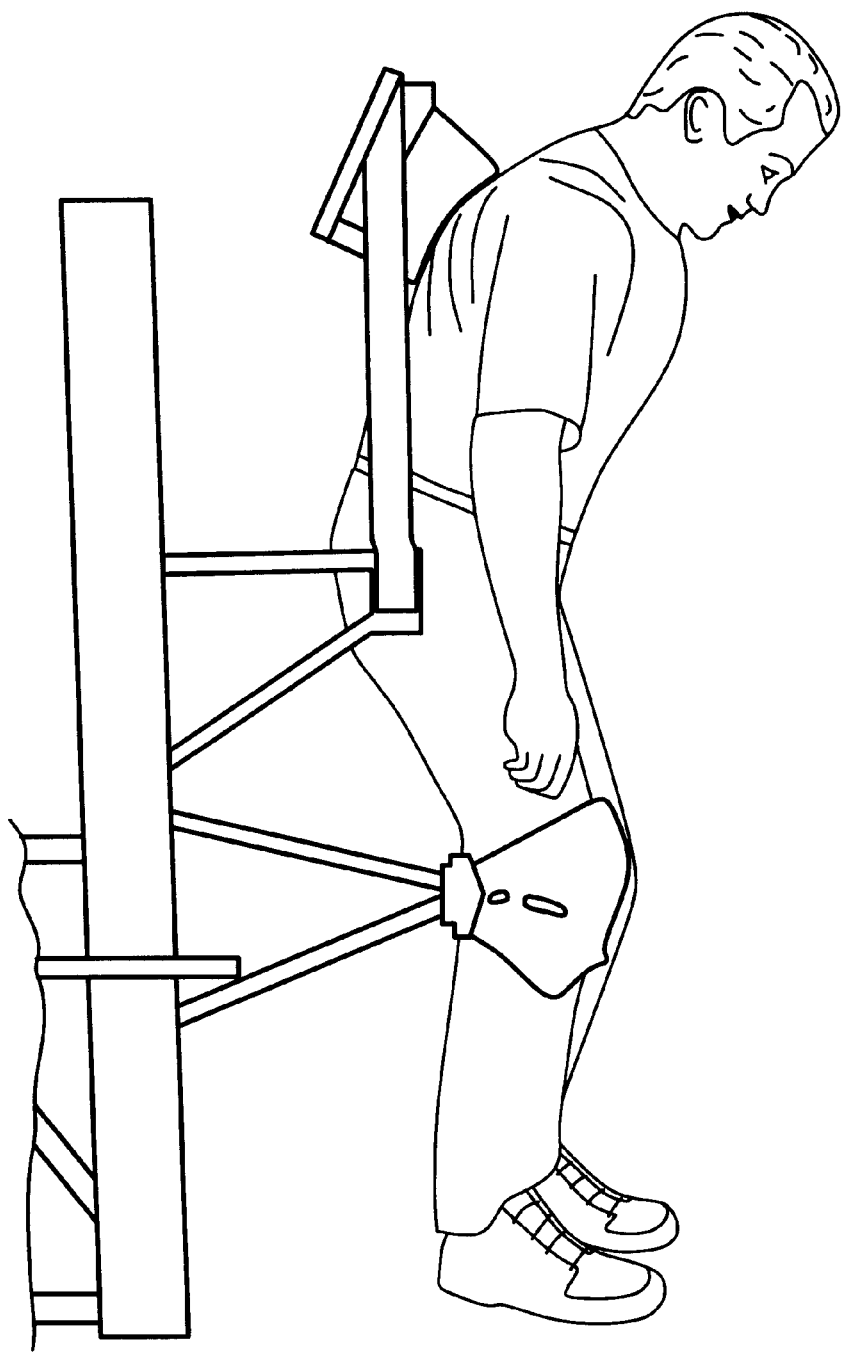
FIG. 37 is a side view of the outer frame subsection and the adjustable seat subsection shown in FIG. 36 used in the isokinetic testing machine in accordance with the present invention with an individual positioned in the outer frame subsection for conducting the trunk isokinetic test.
Figure 38:
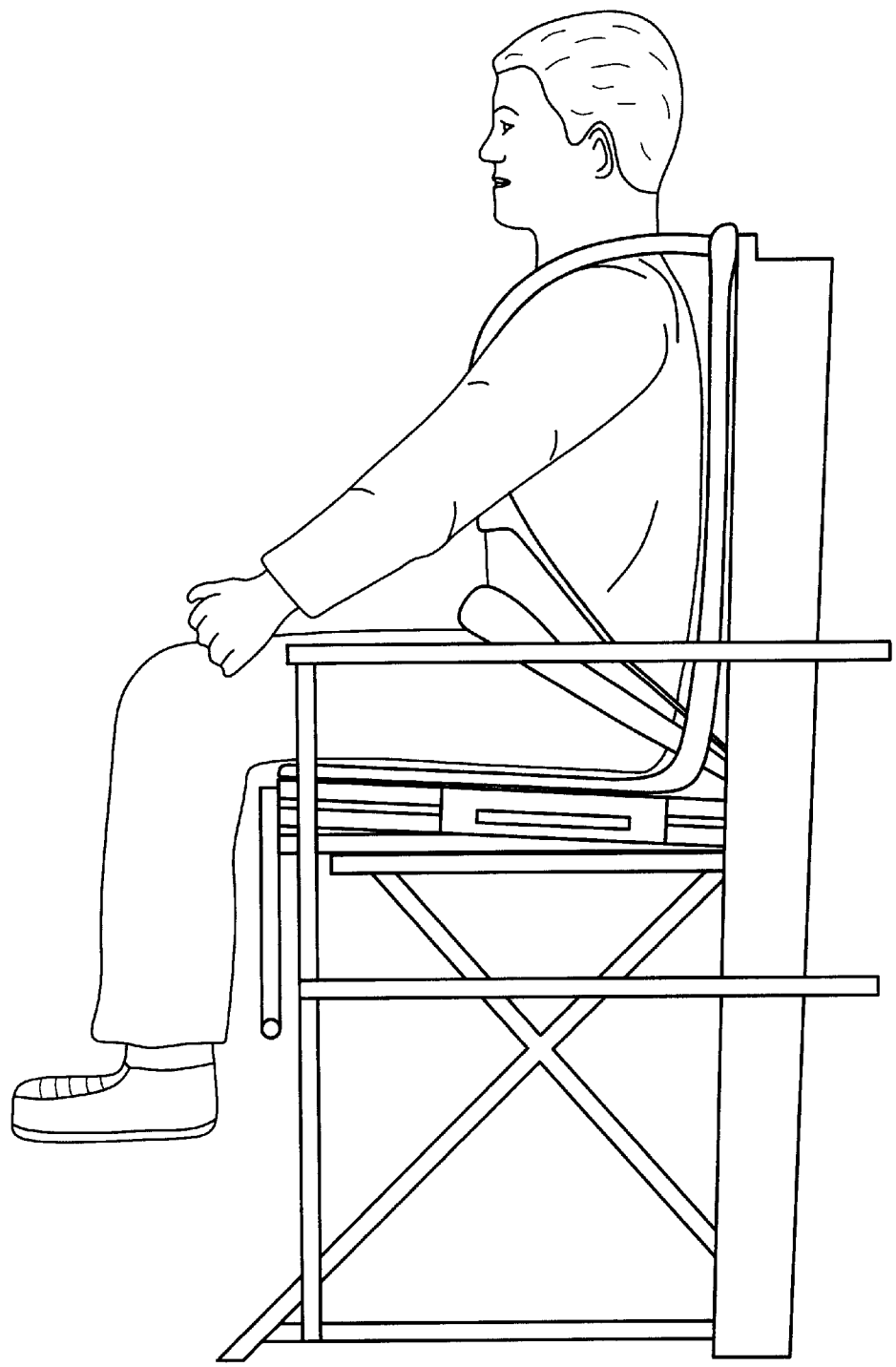
FIG. 38 is a side view of the outer frame subsection and the adjustable seat subsection shown in FIG. 36 used in the isokinetic testing machine in accordance with the present invention with an individual positioned in the adjustable seat subsection for arm isokinetic testing.
Figure 39:
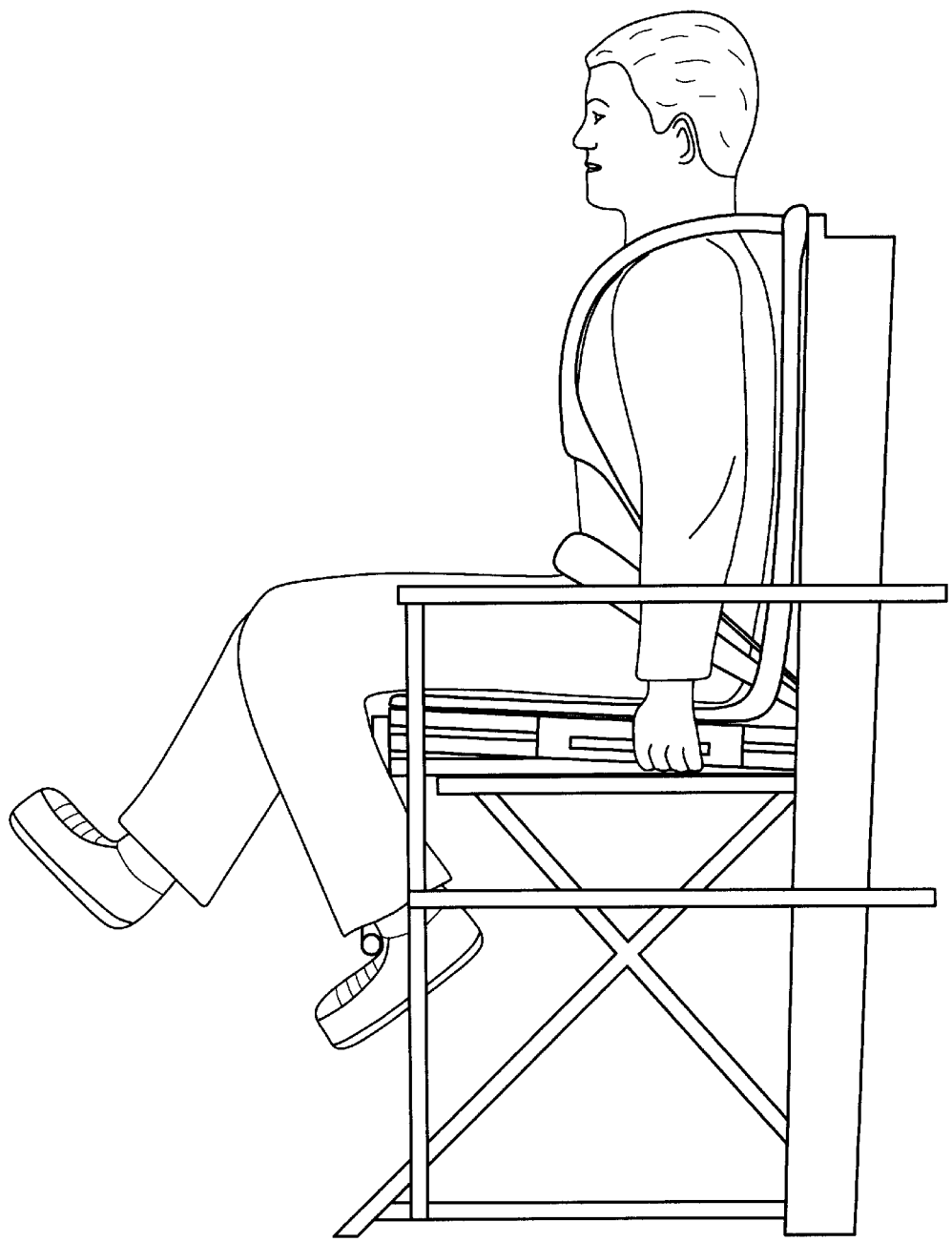
FIG. 39 is a second side view of the outer frame subsection and the adjustable seat subsection shown in FIG. 36 used in the isokinetic testing machine in accordance with the present invention with an individual positioned in the adjustable seat subsection for leg isokinetic testing.

Next, referring to FIGS. 36 through 39, which show a first front perspective view of an outer frame subsection and an adjustable seat subsection fabricated from aluminum used in the isokinetic testing machine in accordance with the present invention, side view of the outer frame subsection and the adjustable seat subsection shown in FIG. 36 used in the isokinetic testing machine in accordance with the present invention with an individual positioned in the outer frame subsection for conducting the trunk isokinetic test, a side view of the outer frame subsection and the adjustable seat subsection shown in FIG. 36 used in the isokinetic testing machine in accordance with the present invention with an individual positioned in the adjustable seat subsection for arm isokinetic testing, a side view of the outer frame subsection and the adjustable seat subsection shown in FIG. 36 used in the isokinetic testing machine in accordance with the present invention with an individual positioned in the adjustable seat subsection for leg isokinetic testing, respectively, adjustable seat subsection 32 preferably includes wing members 56 which are removably attached on the sides of adjustable seat subsection 32. Wing members 56 preferably each include handle 58 to provide additional thigh support for conducting the leg isokinetic tests. Removal of wing members 56 provides room for arm swing during the arm isokinetic tests.

Although the present invention has been described above in detail, the same is by way of illustration and example only and is not to be taken as a limitation on the present invention. It is apparent to those having a level of ordinary skill in the relevant art that other variations and modifications in isokinetic testing machine in accordance with the present invention, as described and shown herein, could be readily made using the teachings of the present invention. For example, other aspects of the isokinetic testing machine in accordance with the present invention are shown in the drawings. Accordingly, the scope and content of the present invention are to be defined only by the terms of the appended claims.

What is claimed is:

1. An isokinetic testing machine, comprising:
    an adjustable seat subsection having a substantially horizontal seat member and a substantially vertical back member, said vertical back member of said adjustable seat subsection including an isokinetic trunk testing station; and
    a dynamometer subsection attached to said adjustable seat subsection in a plurality of different configurations, said dynamometer subsection including a dynamometer subsection support assembly and a dynamometer, wherein the configuration of said dynamometer subsection is selectively chosen to position said dynamometer to permit isokinetic tests to be selectively performed on at least the left leg, the right leg, the left arm, the right arm and the trunk of an individual to be evaluated.

2. The isokinetic testing machine in accordance with claim 1, wherein said adjustable seat subsection, said dynamometer subsection support assembly and said dynamometer are fabricated as three (3) separate independent components and said dynamometer subsection support assembly is removably attached to said adjustable seat subsection.

3. The isokinetic testing machine in accordance with claim 1, wherein said adjustable seat subsection includes a first side member and a second side member attached to the rear of said horizontal seat member.

4. The isokinetic testing machine in accordance with claim 3, wherein said adjustable seat subsection includes a horizontal top member positioned on the top of said vertical back member.

5. The isokinetic testing machine in accordance with claim 3, wherein at least one of said horizontal seat member and said vertical back member includes pads or cushioning to enhance the comfort of the individual to be evaluated.

6. The isokinetic testing machine in accordance with claim 3, wherein both of said horizontal seat member and said vertical back member include pads or cushioning to enhance the comfort of the individual to be evaluated.

7. The isokinetic testing machine in accordance with claim 3, wherein said adjustable seat subsection includes a base member which supports said first side member, said second side member and said vertical back member.

8. The isokinetic testing machine in accordance with claim 7, wherein said adjustable seat subsection includes a vertical back subassembly having a portion of said base member and said vertical back member and a horizontal seat subassembly including the remaining portion of said base member, said first side member, said second side member and said horizontal seat member.

9. The isokinetic testing machine in accordance with claim 3, wherein said adjustable seat subsection includes at least one wing member which is capable of being removably attached to at least one of said first side member and said second side member, said wing members including a handle to provide additional thigh support to facilitate the isokinetic testing of the legs of an individual to be evaluated.

10. The isokinetic testing machine in accordance with claim 3, wherein said adjustable seat subsection includes a first wing member which is capable of being removably attached to said first side member and a second wing member which is capable of being removably attached to said second side member, said first wing member and said second wing member each including a handle to provide additional thigh support to facilitate the isokinetic testing of the legs of an individual to be evaluated.

11. The isokinetic testing machine in accordance with claim 1, wherein said dynamometer subsection support assembly includes a harness strap and at least one restraining clamp to facilitate fixing said dynamometer in position relative to said adjustable seat subsection.

12. The isokinetic testing machine in accordance with claim 1, wherein said dynamometer subsection support assembly includes a lower horizontally extending support rail, a upper horizontally extending support rail and a vertically extending dynamometer support plate, said vertically extending dynamometer support plate is positioned between said lower horizontally extending support rail and said upper horizontally extending support rail and is slidable relative to said lower horizontally extending support rail and said upper horizontally extending support rail.

13. The isokinetic testing machine in accordance with claim 12, wherein said lower horizontally extending support rail includes a plurality of wheels to facilitate the movement of said dynamometer subsection.

14. The isokinetic testing machine in accordance with claim 1, wherein at least one of said dynamometer subsection support assembly and said adjustable seat subsection includes structural supports to enhance the structural integrity of at least one of said dynamometer subsection support assembly and said adjustable seat subsection.

15. The isokinetic testing machine in accordance with claim 1, wherein at each of said dynamometer subsection support assembly and said adjustable seat subsection include structural supports to enhance the structural integrity of said dynamometer subsection support assembly and said adjustable seat subsection.

16. The isokinetic testing machine in accordance with claim 1, wherein said dynamometer subsection support assembly and said adjustable seat subsection are fabricated from aluminum.

17. The isokinetic testing machine in accordance with claim 1, wherein said dynamometer subsection support assembly, said dynamometer and said adjustable seat subsection are capable of being disconnected for transportation and storage and are also capable of being joined together to conduct isokinetic tests on the individual to be evaluated.

18. The isokinetic testing machine in accordance with claim 17, wherein said dynamometer subsection support assembly, said dynamometer and said adjustable seat subsection are removably joined together using mechanical fasteners.

19. The isokinetic testing machine in accordance with claim 17, wherein said dynamometer subsection support assembly, said dynamometer and said adjustable seat subsection are removably joined together using threaded mechanical fasteners.

20. An isokinetic testing machine, comprising:

an adjustable seat subsection having a seating portion and a back member; and a dynamometer subsection selectively attached to said adjustable seat subsection, said dynamometer subsection including a dynamometer subsection support assembly and a dynamometer to permit isokinetic tests to be performed on at least the left leg, the right leg, the left arm and the right arm of an individual to be evaluated, said dynamometer subsection support assembly allows said dynamometer to be moved and positioned in relation to said adjustable seat subsection along each side of said adjustable seat subsection.

21. A portable isokinetic testing machine, comprising plural subsections which are selectively combined with one another to form an isokinetic testing machine for permitting selective isokinetic tests on at least a plurality of body portions, wherein said plurality of subsections include at least an adjustable seat subsection and a dynamometer subsection, wherein the configuration of the dynamometer subsection is modifiable such that when combined with another subsection of the machine, will provide for a plurality of isokinetic tests to be selectively performed.

* * * * *